United States Patent [19]

Franks

[11] 4,128,765
[45] Dec. 5, 1978

[54] ION BEAM MACHINING TECHNIQUES AND APPARATUS

[76] Inventor: Joseph Franks, 26 Hamilton Rd., London, England

[21] Appl. No.: 736,954

[22] Filed: Oct. 29, 1976

[51] Int. Cl.² .............................................. G21K 5/06
[52] U.S. Cl. ................................... 250/442; 250/398; 250/491
[58] Field of Search ................... 250/440, 442, 492 A, 250/451, 456, 491, 423, 398, 311; 219/121 EB, 121 EM; 156/643

[56] References Cited

U.S. PATENT DOCUMENTS

| | | | |
|---|---|---|---|
| 3,629,577 | 12/1971 | Weber et al. | 250/442 |
| 3,719,776 | 3/1973 | Fujiyas et al. | 250/442 |
| 3,757,118 | 9/1973 | Hodge et al. | 250/442 |

*Primary Examiner*—Alfred E. Smith
*Assistant Examiner*—Anderson B. C.
*Attorney, Agent, or Firm*—Blanchard, Flynn, Thiel, Boutell & Tanis

[57] ABSTRACT

Method for producing specimens suitable for examination by electron microscopy techniques in accordance with which at least one ion beam from an ion source is directed onto a specimen while effecting relative rotation between the ion source(s) and the specimen and simultaneously varying the angle of incidence of ion beam(s) whereby the angle of incidence of the ion beam(s) on the specimen is varied in a random manner. The ion source(s) may remain stationary while rotating and rocking the specimen or the ion source(s) may be rocked and the specimen rotated and rocked or the specimen may remain stationary while rocking and rotating the ion source(s) or both the source(s) and the specimen may be rotated and rocked. In apparatus for carrying out the method of the invention there is provided specimen support means and means for rotating same, at least one ion source adapted to direct at least one ion beam onto the specimen and means for varying the angle of incidence of the ion beam(s) on the surface of the specimen.

20 Claims, 3 Drawing Figures

ION BEAM MACHINING TECHNIQUES AND APPARATUS

This invention relates generally to ion beam machining techniques where it is important to minimise the occurrence of artifacts introduced during the etching process. Specific examples where these techniques are utilised are in the preparation of specimens for examination by transmission electron microscopy or by scanning electron microscopy.

When utilising transmission electron microscopy techniques for examining specimens it is required that the specimens be thinned sufficiently to allow electrons to penetrate to form an image. One technique proposed heretofore for producing thin specimens is based on ion beam erosion of the specimens and it has been proposed to utilise equipment whereby a specimen may be irradiated from one or both sides by ion beams.

When utilising scanning electron microscopy techniques for examining specimens it is required that surface features and structures are made apparent by their scattering effect on the incidence electrons. A technique used to reveal these features and structures is to irradiate the specimen with ions.

In preparing a specimen utilising the ion beam erosion technique for transmission electron microscopy, it is important to ensure that the specimen is eroded in such a manner that a thin even layer of as large an extent as possible is produced and to achieve this it has been proposed to rotate the specimen during the thinning process. In the methods proposed heretofore the ion beam or beams are, however, merely set to an angle of incidence which has been determined by experience to introduce the least irregularities in the surface specimen. The known methods and equipment, however, still leave undesirable irregularities in the prepared specimen.

It is an object of the present invention to provide a method and apparatus which provides for the production of specimens in which undesirable surface irregularities are minimised to provide specimens having good surface smoothness as compared to those obtainable with the previously known methods and apparatus.

Accordingly the present invention contemplates a method for the preparation of specimens suitable for examination by electron microscopy techniques in which at least one ion beam from at least one ion source is directed onto the specimen while effecting relative rotation between the ion source(s) and the specimen and simultaneously varying the angle of incidence of said at least one ion beam whereby as far as possible the angle of incidence of said at least one ion beam on the specimen is varied in a random manner.

The angle of incidence of the ion beam or beams may be varied in any suitable manner as for example, by rocking the ion source or sources to and fro if the plane of the specimen is fixed or by rocking the specimen holder to and fro if the position of each ion source is fixed or by moving to and fro both the specimen holder and each ion source. Preferably each ion source is rocked with the specimen holder remaining in a fixed plane which allows the specimen to be conveniently observed with a microscope.

Effective results have been obtained with each ion source being rocked between an angle of, for example, 0° (glancing angle) and 90°.

In preparing a specimen for examination utilising the ion beam erosion technique of scanning electron microscopy it is important that etching artifacts are minimised to avoid confusion with the real surface structure. This again may be achieved by rotating the specimen and rocking the source.

The invention also contemplates the provision of apparatus for ion beam machining of specimens for electron beam microscopy, which apparatus includes means, such as a specimen holder, means for mounting the specimen, means for rotating the specimen holder, at least one ion source, and means for directing an ion beam from each ion source onto a surface of the specimen and for varying the angle of incidence of the ion beam or beams on the surface of the specimen.

The means for varying the angle of incidence of each ion beam on the surface of the specimen preferably comprises means for rocking each ion source through a set angle with the plane of the specimen being fixed. Alternatively the ion source(s) may be fixed and the specimen rotated.

The means for varying the angle of incidence of each ion beam may comprise means for locking the ion source(s), or means for rocking the specimen if the position of each ion source is fixed or may comprise a combination of means for rocking each ion source and means for rocking the specimen.

Other features which may be included in accordance with the invention will be described hereinafter and referred to in the appended claims.

The invention will now be more particularly described with reference to embodiments thereof shown, by way of example, in the accompanying drawings, in which.

Figure 1:
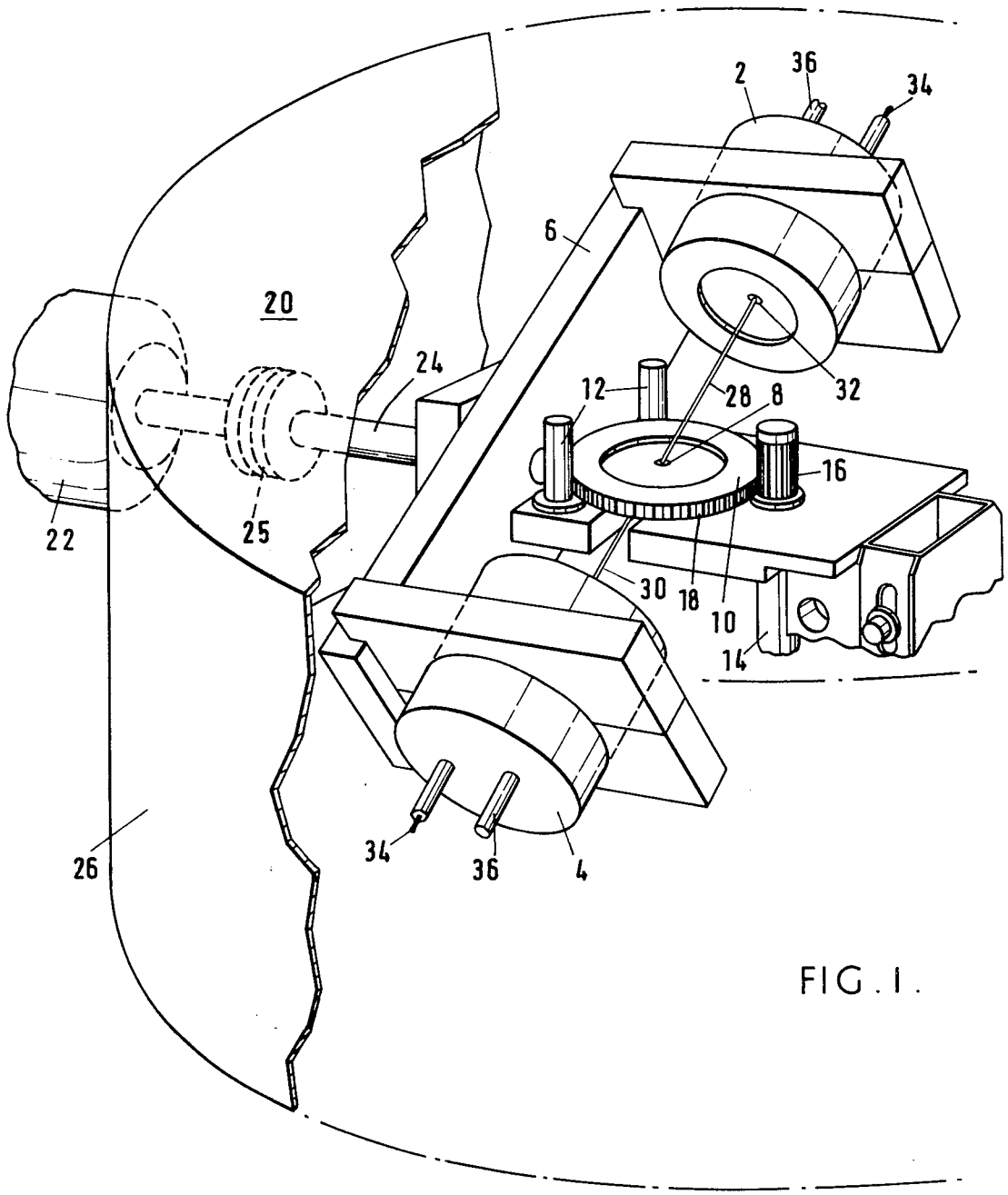
FIG. 1 is a perspective view of the principal parts of an ion thinning unit rotatable within a specimen chamber, part of the wall of which is removed in the drawings to show the ion source assembly and the specimen stage with associated drive mechanism.
Figure 2:
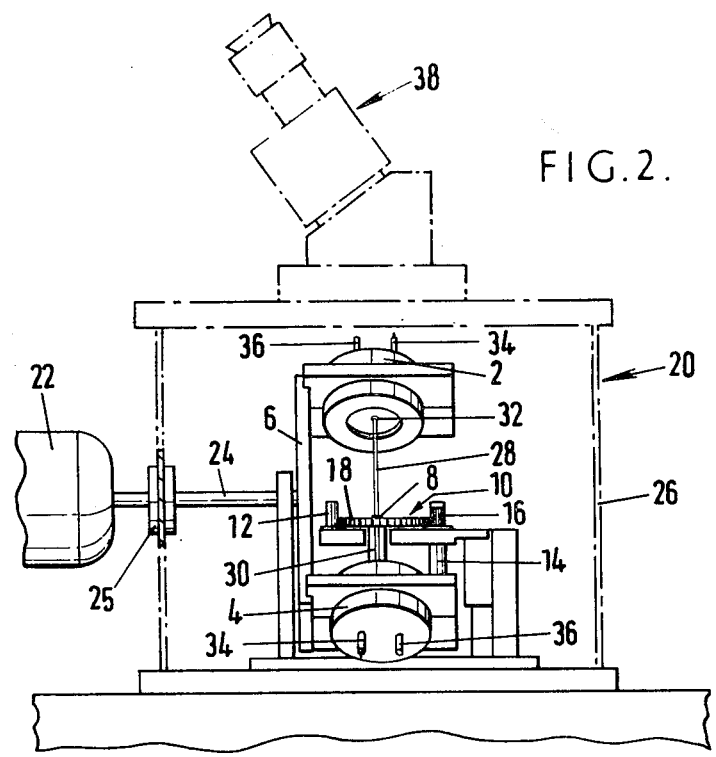
FIG. 2 is a view in side elevation of the ion thinning unit of FIG. 1.

Referring to FIGS. 1 and 2, 2 and 4 are saddle-field ion sources which may suitably be of the type disclosed in U.S. Pat. No. 3,944,873 issued Mar. 16, 1976 and which, because of their compact structure, can readily be mounted on a rotatable arm generally designated 6. The specimen 8 is mounted on a rotatable specimen platform 10 supported on rollers 12 and driven by shaft 14 of a motor (not shown) through a gear wheel 16 which meshes with the peripheral edge 18 of the platform 10.

The ion source assembly and the specimen platform with associated drive mechanisms are mounted inside a vacuum chamber 20 which is maintained at a suitable vacuum as, for example, by a pumping system (not shown) utilising a diffusion pump which can be supplied with the apparatus or the apparatus may be supplied ready for connection to a suitable pumping system.

The centre of the rotatable specimen platform 10 is located on the axis of the pivot of the arm 6. The arm 6 is driven by a servo-motor 22 located outside the vacuum chamber 20 through a rotary shaft 24 which extends through a vacuum seal 25 in the wall 26 of the chamber. The rotatable arm 6 may be set at any angle relative to the plane of the specimen platform 10 from 0°

(glancing incidence) through 90° (normal) to 180° and may be rocked at any amplitude between these limits.

If the arm 6 supporting the source(s) is set at a fixed angle, then the angle of incidence of the beam at a point P on the surface of the rotating specimen will vary with an amplitude depending on distance of P from the centre of rotation of the specimen. At the centre of rotation there will be no change in the angle of incidence. At a point remote from the centre, the angle of incidence will be the same each time the specimen has completed one revolution. The angle of incidence of the beam at P therefore varies in a regular manner. Under these conditions ion etching frequently produces hummock shaped artifacts. It has been found that the formation of such artifacts can be prevented by randomising the angle of incidence, i.e. if after point P has completed a revolution the angle of incidence of the ion beam has changed with respect to the initial angle of incidence. This can be achieved by rocking the arm 6 while the specimen platform rotates; it is of course important that the motion of arm 6 is not synchronised with that of the rotating platform.

The ion sources 2 and 4 are preferably fine beam ion sources producing beams 28 and 30 of about 1.5 mm diameter from cathode apertures 32 which beams pass through the centre of the rotatable specimen platform 10 on which the specimen is situated. Electrical powder and gas for operation of the ion beam sources are supplied to the ion beam sources via leads 34 and conduits 36 respectively which are led into the vacuum chamber 20 through ports (not shown) in the wall 26 thereof.

During the thinning process material is controllably removed from either side of the specimen by exposure to the ion beams from the two diametrically opposed ion sources.

The specimen is illuminated and may be observed during processing through a binocular microscope 38 mounted above the vacuum chamber.

Figure 3:
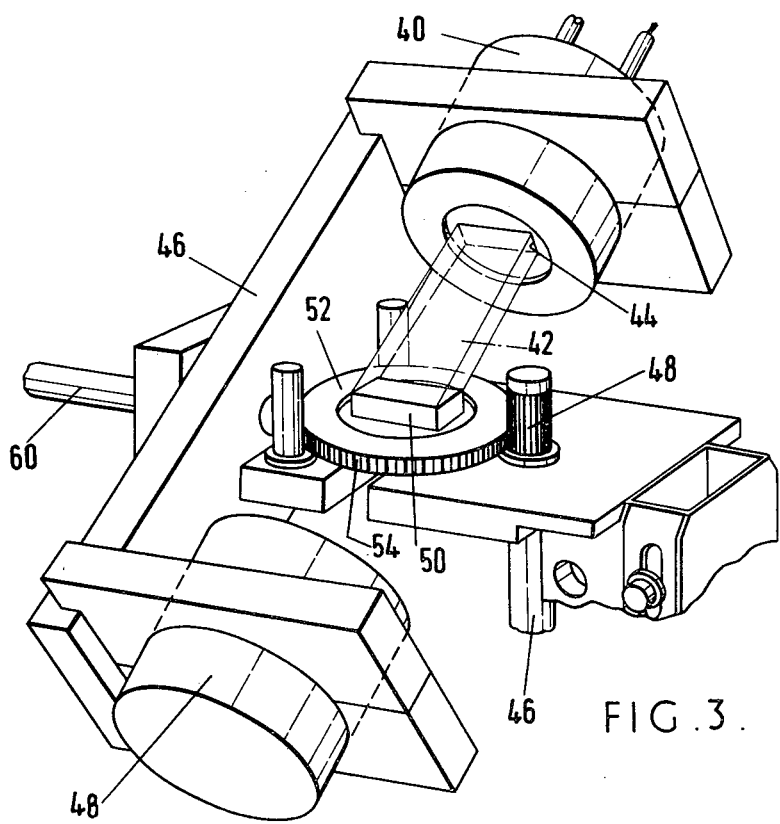
FIG. 3 is a perspective view of the ion source assembly and specimen stage, with associated drive mechanisms, of an ion surface preparation unit.

An example of an ion surface preparation unit is shown in FIG. 3 in which 40 is a wide beam saddle-field ion source emitting a beam 42 about 1 cm long from cathode aperture 44. The beam 42 diverges normal to the length of the aperture 44 at an angle of about 15°, there being little divergence along the cathode aperture. The ion source 40 is mounted on one end of the rotatable arm 46 and a counterbalance 48 is mounted on the opposite end of the arm. A specimen 50 is mounted on a rotatable specimen platform 52 having a toothed periphery 54 and which is driven by shaft 46 of a motor (not shown) through a gear 48 which meshes with the toothed periphery 54 of the platform in the same manner as in the ion thinning unit described hereinbefore with reference to FIGS. 1 and 2. The arm 46 is also driven in the same manner as in the previously described embodiments by means of a suitable servomotor (not shown) through a shaft 60. The surface of the specimen does not coincide with the axis of the pivot of the rotatable arm, so that when the arm 46 rocks, the intense central region of the beam travels over the surface of the specimen thus ensuring an even rate of etching.

Although in the illustrated embodiments of the invention described in detail in the foregoing involve rotating the specimen about a perpendicular axis while rocking the ion source(s), it will be appreciated that the ion source(s) could remain stationary and the specimen could be rotated and rocked; or the ion source(s) could be rotated about the specimen and the specimen rocked; or the specimen could remain stationary while the ion source(s) could be rocked, while rotating about an axis through the centre of the specimen and normal to it, or both the ion source(s) and the specimen could be rotated, or the ion source(s) could be either rocked or rotated while rocking and rotating the specimen; or the ion source(s) could be rocked and rotated while rocking the specimen.

In all cases the effect is to vary the angle of incidence of the ion beam or beams on the specimen in order to randomise the angle of incidence of each ion beam on the specimen.

I claim:

1. A method of ion beam machining for the preparation of specimens to be examined by electron microscopy techniques comprising directing at least one ion beam from an ion source onto a specimen while effecting relative rotation between the ion source and the specimen and simultaneously varying the angle of incidence of said at least one ion beam on said specimen with such angle varying in a random manner with respect to said relative rotation of said ion source and said specimen.

2. A method as claimed in claim 1, in which a diametrically opposed pair of said ion beams from a pair of ion sources are directed onto opposite sides of the specimen.

3. A method as claimed in claim 1, in which the specimen remains stationary and said angle of incidence is varied by rocking each said ion source through a predetermined angle and rotating each said source about the specimen.

4. A method as claimed in claim 1, wherein the position of each ion source remains stationary and said angle of incidence is varied by rocking and rotating the specimen about its axis through a predetermined angle, and rotating the specimen.

5. A method as claimed in claim 1, wherein the said angle of incidence is varied by rotating each said ion source about the specimen and rocking the specimen.

6. A method as claimed in claim 1, wherein the said angle of incidence is varied by rocking and rotating both the specimen and each said ion source.

7. A method as claimed in claim 1, wherein there are two of said ion sources each of which is a fine beam source.

8. A method as claimed in claim 1, wherein there is a single ion source which is a wide beam source.

9. Apparatus for ion beam machining of electron microscopy specimens comprising rotatable means for supporting a specimen, means actuable for rotating said specimen supporting means, at least one ion source adapted to direct at least one ion beam onto said specimen, means supporting said ion source for relative movement between the plane of rotation of said specimen support means and said ion source, and means nonsynchronized with said specimen support rotating means and actuable for varying the angle of incidence of said at least one ion beam on the surface of said specimen to avoid the same angle of incidence of said beam on a rotating point on said specimen at the end of successive revolutions of said specimen.

10. Apparatus as claimed in claim 9, wherein there are two diametrically opposed said ion sources, the ion beams from which are adapted to be directed on to opposite surfaces of said specimen.

11. Apparatus as claimed in claim 9, wherein said means for varying the angle of incidence of each said ion beam comprises means for rocking each ion source through a predetermined angle and rotating each ion source about the specimen while the specimen remains stationary.

12. Apparatus as claimed in claim 9, wherein said means for varying the angle of incidence of each ion beam comprises means for rocking and rotating the specimen supporting means while maintaining each said ion source in a fixed position.

13. Apparatus as claimed in claim 9, wherein said means for varying the angle of incidence of each ion beam comprises means for rotating each ion source about the specimen and rocking the specimen supporting means.

14. Apparatus as claimed in claim 9, wherein said means for varying the angle of incidence of each ion beam comprises means for rocking each ion source and means for rocking and rotating the specimen supporting means about their respective axes.

15. Apparatus as claimed in claim 9, wherein said means for varying the angle of incidence of each ion beam comprises means for rocking and rotating each ion source and means for rocking and rotating the specimen supporting means about their respective axes.

16. A method as claimed in claim 1, in which the specimen is rotated and the angle of incidence is varied by rocking each said ion source through a predetermined angle about said specimen during said specimen rotation.

17. A method as claimed in claim 1, in which the angle of incidence is so varied that it differs at a given point on the specimen at the end of each relative revolution between said ion source and specimen, so as to avoid repeating the same angle of incidence for a given relative rotational position between said specimen and said ion source.

18. A method as claimed in claim 1, including maintaining a state of nonsynchronism between said varying of said angle of incidence and said relative rotation between said ion source and specimen, to avoid repeating the same angle of incidence for a given relative rotational position between said specimen and ion source.

19. Apparatus as claimed in claim 9, in which said specimen supporting means is a rotatably supported platform, said means for rotating said specimen supporting means comprising a first motor in rotational driving connection with said platform, said angle varying means including an ion beam source support capable of at least limited rotary motion through a range of beam angles of incidence on said specimen surface, and a second motor nonsynchronized with said first motor and in rotative driving connection with said ion beam source support.

20. Apparatus as claimed in claim 19, in which said second motor is a servo motor actuable to rock said ion beam within a preselected angular range and along a plane transverse to the plane of rotation of said platform.

* * * * *